United States Patent [19]
Tsunekawa et al.

[11] 4,442,239
[45] Apr. 10, 1984

[54] PHOSPHATE DERIVATIVES, PROCESS FOR PRODUCING PHOSPHATE DERIVATIVES AND FILLERS FOR HUMAN HARD TISSUES CONTAINING THE SAME

[75] Inventors: Masayoshi Tsunekawa; Shinzo Yoshida; Tamotsu Komura, all of Kawanishi, Japan

[73] Assignee: Sankin Industry Co., Ltd., Osaka, Japan

[21] Appl. No.: 347,429

[22] Filed: Feb. 10, 1982

[30] Foreign Application Priority Data

Feb. 12, 1981 [JP] Japan .................. 56-19520

[51] Int. Cl.³ .............. C08F 136/14; C08F 136/22; C08F 230/02; A61K 5/00
[52] U.S. Cl. ........................ 523/116; 526/277; 260/930; 260/964; 524/730; 524/789
[58] Field of Search .......... 526/277; 528/950; 260/928, 929, 930, 964

[56] References Cited

U.S. PATENT DOCUMENTS

| 2,643,265 | 6/1953 | Toy | 260/930 |
| 2,791,574 | 5/1957 | Tanham | 526/277 |
| 3,346,545 | 10/1967 | Jehm | 526/277 |
| 3,754,972 | 8/1973 | DeMajistie | 260/928 |
| 3,761,593 | 9/1973 | Ginsha | 260/930 |
| 3,855,364 | 12/1974 | Steckler | 260/952 |
| 3,936,514 | 2/1976 | Shim | 260/929 |
| 3,946,092 | 3/1976 | Nachbur et al. | 260/930 |
| 3,950,457 | 4/1976 | D'Alelio | 260/928 |
| 4,259,117 | 3/1981 | Tamauchi | 526/277 |

FOREIGN PATENT DOCUMENTS

| 127 | 1/1979 | European Pat. Off. |
| 58483 | 8/1982 | European Pat. Off. | 526/277 |
| 2711234 | 9/1977 | Fed. Rep. of Germany | 528/950 |
| 688372 | 3/1953 | United Kingdom |
| 892405 | 3/1962 | United Kingdom |
| 1076796 | 7/1967 | United Kingdom |
| 1310920 | 3/1973 | United Kingdom |
| 1377978 | 12/1974 | United Kingdom |
| 1393545 | 5/1975 | United Kingdom |
| 2093458 | 2/1982 | United Kingdom | 260/930 |

OTHER PUBLICATIONS

Kopollasoff & Maies "Organic Phosphons Compounds", vol. 6, Willey—Interscience (1973).
p. 411, compounds 5, 6, 10, 12; p. 412, compounds 1, 8, 9, 10.
p. 454, compound 6, p. 455, compounds 2, 25.

Primary Examiner—Joseph L. Schofer
Assistant Examiner—Peter F. Kulkosky
Attorney, Agent, or Firm—Oblon, Fisher, Spivak, McClelland & Maier

[57] ABSTRACT

Phosphate derivatives represented by the formula

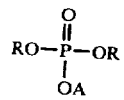

wherein R represents a group containing at least one reactive double bond and A represents a group which may optionally contain reactive double bonds are disclosed. The phosphate derivatives of the present invention have at least two reactive double bonds, and polymers prepared from these phosphate derivatives in the presence or absence of other polymerizable monomers are useful as fillers for human hard tissues such as bones and teeth.

19 Claims, No Drawings

PHOSPHATE DERIVATIVES, PROCESS FOR PRODUCING PHOSPHATE DERIVATIVES AND FILLERS FOR HUMAN HARD TISSUES CONTAINING THE SAME

BACKGROUND OF THE INVENTION

1. Field of the Invention

This invention relates to phosphate derivatives useful as fillers for human hard tissues having excellent mechanical strength and handling properties, a process for producing such phosphate derivatives and fillers for human hard tissues obtained from the phosphate derivatives. The term "human hard tissues" as used herein means human bones, teeth and the like. The fillers according to the present invention exhibit excellent properties for reparation of such hard tissues, particularly, they are used as fillers for dental treatment. The present invention as well as conventional techniques relating thereto are therefore described hereinafter mainly with reference to applications in the field of dentistry, but it is to be understood that these descriptions can also be applied to other human hard tissues and that the utility according to the present invention is not limited to the field of dentistry.

2. Description of the Prior Art

Hitherto, various filler materials for use in dentistry have been known and, of these conventional fillers, a so-called composite resin filler comprising polymerizable monomers and inorganic fillers has been widely used in reparation of front tooth because of its excellent mechanical strength, appearance, operability, etc. Also, such composite resin fillers are now used for reparation of temporary molars.

However, since molars are generally subjected to extremely high occlusal pressure, the fillers used for reparation of molars must have improved mechanical strength such as compression strength, bending strength and the like sufficient to endure such pressure and, therefore, conventional fillers could not be applied to molars having occlusal surfaces. One method has been known for improving the mechanical strength of composite resin fillers by using finely divided inorganic fillers and extensive studies have been made from this standpoint.

On the other hand, U.S. Pat. Nos. 3,066,112 and 3,179,623 disclose a glycidyl methacrylate derivative of bisphenol A (hereinafter abbreviated as "Bis-GMA") represented by the formula

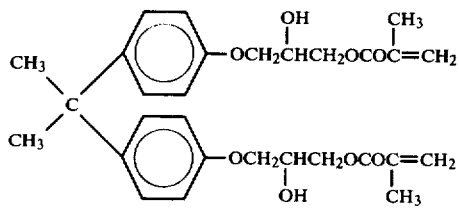

as a polymerizable monomer which provides an extremely hard resin and hence the above monomer has been mainly used as a composit resin filler. No polymeric monomers having properties superior to Bis-GMA have been developed thus far.

However, Bis-GMA has a defect in that it is very difficult to handle because of its highly viscous property unless it is diluted with a reactive diluent such as methyl methacrylate, ethylene glycol dimethacrylate, triethylene glycol dimethacrylate and the like. The use of these reactive diluents may cause other problems, i.e., poor moisture resistance and decreased mechanical strength of the cured filler by absorbing a large amount of water. In addition, as the most basic problem, the above reactive diluents are strongly irritative to the affected part of patients since they have a relatively low molecular weight and thus are permeable to dental pulp tissues. It is therefore highly desirable to develop monomers which require only a small amount of these reactive diluents.

Also, in the conventional composit resin fillers, finely divided inorganic fillers are incorporated into polymerizable monomers and other components in order to improve the mechanical strength thereof, but it is also preferred to use polymerizable monomers having a viscosity lower than Bis-GMA and having a crosslinking property higher than Bis-GMA as a monomer component of the composite resin filler.

As a result of extensive studies, the present inventors previously proposed a compound which satisfies the above requirements, as disclosed in Japanese Patent Application Nos. 114995/80, 114996/80 and 133234/80, but it is still desirable to develop monomers having improved mechanical properties and operability. More specifically, the compounds disclosed in the above three Japanese patent applications are pyrophosphate derivatives having polymerizable double bonds such as those present in alkenyloxy, acryloyloxy(lower)alkyl, methacryloyloxy(lower)alkyl groups. These pyrophosphate derivatives exhibit satisfactory adhesive properties for bones and teeth, but appear to require further improvements as a filler for reparatory use.

SUMMARY OF THE INVENTION

The present invention aims at improvements of the conventional fillers used for human hard tissues.

An object of the present invention is therefore to provide a novel type of polymerizable monomers having no disadvantages of the conventional fillers as described above, in particular, to provide polymerizable monomers which can be easily handled without using a low molecular weight reactive diluent.

Another object of the present invention is to provide a polymer having a satisfactory mechanical strength for use in the particular field of mending treatment of human hard tissues as well as a polymerizable monomer for producing such polymers.

A further object of the present invention is to provide a process for effectively producing the above monomer.

These objects and the effects obtained by the present invention will be apparent from the detailed disclosure set forth below.

DETAILED DESCRIPTION OF THE INVENTION

The polymerizable monomer according to the present invention is a phosphate represented by the formula (I)

wherein A represents an acyclic hydrocarbon or an aryl group, each of which may be substituted with one or more substituents selected from the group consisting of an alkenyl group, an acryloyloxy group, a methacryloyloxy, an aryl group, a halogen atom, an alkyl group, an alkoxy group, a hydroxy group and a group of the formula

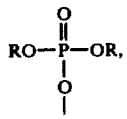

in which each of the substituents may further be substituted with one or more aryl groups or halogen atoms, and any aryl group as a substituent of the group A may be substituted with a substituent selected from the group consisting of an alkenyl group, an acryloyloxy group, a methacryloyloxy group and a group of the formula

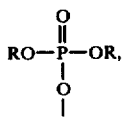

and R's may be the same or different and each represents an alkenyl group, an alkenylaryl group, an acryloyloxy(lower)alkyl group, an acryloyloxyaryl group, a methacryloyloxy(lower)alkyl group or a methacryloyloxyaryl group in which the (lower)alkyl group and aryl group may be substituted with a halogen atom.

The phosphate derivative represented by the formula (I) above can be prepared according to the following reaction scheme:

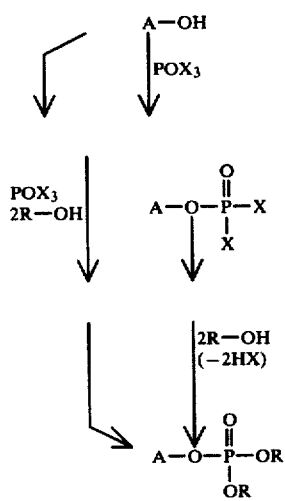

wherein A and Z are as defined above, and X represents a halogen atom.

The groups A and R in the formula (I) are hereinafter described in greater detail.

Examples of alkenyl represented by R include unsaturated acyclic hydrocarbon residual groups having 2 to 6 carbon atoms such as vinyl, allyl, isopropenyl, 2-butenyl, 2-pentenyl, 2-hexenyl and the like. Examples of (lower)alkyl in the group R are straight chain or branched chain saturated acyclic hydrocarbon residual groups having 1 to 6 carbon atoms such as methyl, ethyl, propyl, isopropyl, n-butyl, tert-butyl, pentyl, hexyl and the like. Examples of aryl in the group R are aromatic residual groups such as phenyl, 1-naphthyl, 2-naphthyl and the like. Any of the above unsaturated acyclic hydrocarbon residual groups, saturated acyclic hydrocarbon residual groups and aromatic residual groups may be substituted with a halogen atom such as fluorine, chlorine, iodine and bromine.

The group A in the formula (I) represents an acyclic hydrocarbon group or an aryl group, each of which may have substituents as specifically described above, and the moiety —OA, including the substituents which may be present on this moiety, can be represented by the formula $$-OR^1-R^2-R^3-R^4$$

wherein $R^3$ is a third substituent and $R^4$ is a fourth substituent and each of the substituents $R^2$, $R^3$ and $R^4$ can be optionally present. In the above formula, $R^1$ is a substituent connected directly to the oxygen atom of the phosphate, and $R^2$, $R^3$ and $R^4$ are groups substituted for the hydrogen atoms of $R^1$, $R^2$ and $R^3$, respectively. The group A has at least one side chain represented by $R^1$ and includes a wide variety of groups, i.e., from $-OR^1$ to $-OR^1-R^2-R^3-R^4$ which are within the scope of the present invention. Also, it is to be understood that each of the substituents $R^2$, $R^3$ and $R^4$ is not limited to a single group and therefore it may represent a plurality of substituents.

The substituent $R^1$ represents an acyclic hydrocarbon or aryl. Examples of the acyclic hydrocarbon include the saturated hydrocarbons exemplified for the (lower)alkyl described above as well as unsaturated acyclic hydrocarbons. Examples of aryl include phenyl, naphthyl, anthranyl, phenanthryl and the like. Examples of the second substituent represented by $R^2$ include alkenyl as those exemplified for R; acryloyloxy; methacryloyloxy; aryl as exemplified for $R^1$; halogen atom such as fluorine, chlorine, bromine and iodine; lower alkyl such as those exemplified for the (lower)alkyl of R described above; lower alkoxy such as methoxy, ethoxy, propoxy, isopropoxy, n-butoxy, tert-butoxy, pentyloxy, hexyloxy and the like; hydroxy; and a group of the formula

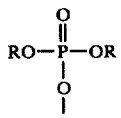

When $R^2$ is either alkenyl, acryloyloxy or methacryloyloxy, $-OR^1-R^2$ represents the same group as $-OR$. Further, examples of the third substituent represented by $R^5$ are aryl or halogen as exemplified above, and examples of the fourth substituent represented by $R^4$ are alkenyl, acryloyloxy, methacryloyloxy and the group represented by the formula

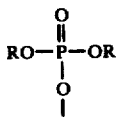

wherein R is as defined above.

The process for producing the compound represented by the formula (I) is hereinafter described in greater detail.

The compound of the formula (I) wherein A represents an acyclic hydrocarbon and is the same as R can be prepared from the compound of the formula (II) in a single reaction step as shown in the above reaction scheme.

More specifically, the reaction proceeds by dissolving the compound (II) and a base in a reaction solvent and reacting the solution with a phosphorus oxyhalide such as phosphorus oxychloride under anhydrous condition and at low temperatures. The reaction solvent can be any organic solvent so long as it does not adversely affect the reaction, and is preferably methylene chloride, chloroform, etc. The base is preferably a tertiary amine such as trialkylamines or pyridine, or a weakly basic inorganic base such as a carbonate. The reaction temperature is preferably about 0° to about 10° C. After completion of the reaction, the desired compound (I) can be isolated from the reaction mixture and purified by conventional procedures.

Alternatively, the compound of the formula (I) wherein A and R represent different groups can be prepared in two reaction steps according to the sequence, Compound (II)→Compound (III)→Compound (I), as shown in the above reaction scheme.

More specifically, the compound (II) is first reacted with a phosphorus oxyhalide, e.g., phosphorus oxychloride under anhydrous condition. In this reaction, phosphorus oxyhalide also serves as a reaction solvent, but the reaction solvent as described above may also be used, if desired. The reaction temperature is not critical, but the reaction is preferably conducted at an elevated temperatures or under heating. The resulting reaction product is a phosphoryl dihalide represented by the formula (III).

The compound (III) thus obtained is then dissolved in a solvent and reacted with an alcoholic compound represented by the formula R—OH under anhydrous condition and in the presence of a base. The reaction can be conducted in a reaction solvent as described above at a temperature of about 0° C. After completion of the reaction, the reaction mixture is washed with hydrochloric acid, potassium hydroxide, etc. and then dried, followed by distilling off the reaction solvent to obtain the desired compound of the formula (I).

The compound of the formula R—OH used in the above reactions is an alcoholic or phenolic compound containing polymerizable functional groups, and the compound of the formula A—OH is an alcoholic or phenolic compound which may optionally contain polymerizable functional groups. Examples of these compounds are shown below.

CH$_2$=CH—CH$_2$—OH

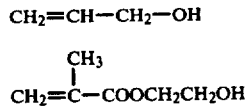

CH$_2$=CH—COOCH$_2$CH$_2$OH

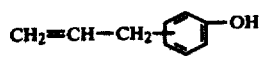

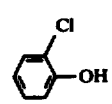

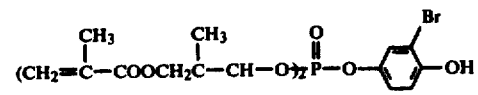

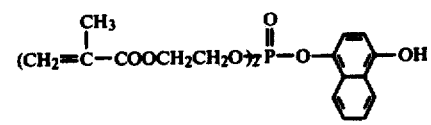

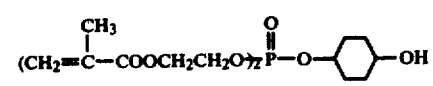

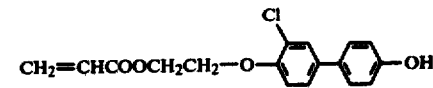

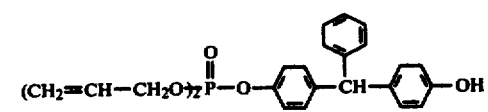

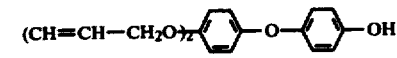

It will be understood that according to the present invention a wide variety of compounds (I) can be prepared freely by appropriately selecting various combinations of these starting materials.

The compounds (I) thus obtained are monomers which can be polymerized via unsaturated bonds contained in the group R or A. The polymerization of such monomers can be effected by light, heat, ultraviolet rays, etc., if necessary, in the presence of polymerization initiators, polymerization promotors, etc.

In using the above compounds (I) as a filler, a curing agent such as benzoyl peroxide and a reaction promoter such as amines are incorporated into the compound (I) to form a filler composition. If desired, inorganic fillers such as quartz powder may be incorporated into the filler composition. The resulting composition (resin binder) can be filled, for example, in a cavity of decayed tooth or broken tooth and then cured. In some instances, a better result can be obtained without inorganic fillers depending upon the size, shape, etc. of the site to which the composition is applied.

In preparing filler compositions, the compound (I) can be used as a monomer in various manners. For example, (1) the monomer of the present invention is applied to the site to be treated and then cured; (2) the monomer of the present invention is mixed with different types of other monomer(s), and the mixture is applied to the site to be treated and then cured; or (3) either a mixture of two or more monomers of the present invention or a mixture of one or more monomers of the present invention and other polymerizable monomers is first polymerized, then the resulting polymer is mixed with monomers which are the same as or different from the monomers used for polymerization, and the mixture is applied to the site to be treated and cured.

In applying the above compounds, the polymer component (excluding inorganic fillers, curing agents, reaction promotors and the like) can be used in various combinations as described below.

First, possible units of combinations include:
A: monomer compound of the present invention,
B: homopolymer prepared from monomer compound A,
C: copolymer prepared from two or more different monomer compounds A, or copolymer prepared from one or more other polymerizable monomers,
D: other polymerizable monomer(s),
E: homopolymer prepared from polymerizable monomer(s) D, and
F: copolymer prepared from different polymerizable monomer(s) D.

Examples of formulations of these units are:
(1) monomer A alone,
(2) a combination of monomer A and one or more units selected from the group consisting of B, C, D, E and F, and
(3) a combination of B and/or C, and D, and optionally E and/or F.

As described above, the application of the resulting fillers is not limited to the use in dentistry.

The properties of the filler according to the present invention are hereinafter described in detail.

The fillers, for example, for dental use as described above must have endurance for a prolonged period of time after they are applied to teeth since otherwise they are easily broken or cracked. The fillers according to the present invention have excellent tensile strength, bending strength, compression strength and elastic coefficient after they are polymerized and exhibit satisfactory endurance against various forces suffered in the oral cavity. Also, the polymerized fillers have excellent anti-abrasive property and sufficient hardness, they are not liable to be injured or worn in the surface of the fillers. Further, the polymerized fillers have low water absorption and thermal expansion properties and, thus, exhibit stable endurance under temperature and moisture conditions in the oral cavity.

In curing the monomers of the present invention, these monomers can be cured in a relatively short period of time and therefore do not give any unpleasant loads to the patients. Also, since the monomers can be gelled in an appropriate period of time and can be easily handled in blending operation, it is not necessary to incorporate low molecular weight reactive diluents to the monomer thereby minimizing irritation to the dental pulp as well as preventing decrease in the mechanical strength of the polymer by absorption of moisture after curing. Further, the polymers obtained after curing exhibit satisfactory physical properties such as compression strength, hardness, anti-abrasion, etc., and thus the monomers of the present invention are useful not only for dental fillers but also as industrial materials in various fields of industry in view of their excellent properties.

The present invention is further illustrated by the following Examples are Preparation Examples, but they are not intended to limit the scope of invention.

EXAMPLE 1

With the dropwise addition of phosphorus oxychloride (16 g) to a methylene chloride solution containing 2-hydroxyethyl acrylate (39 g) and pyridine (36 g), the reaction was conducted at 0° to 10° C. for 2 hours, with constant stirring. After completion of the reaction, the reaction mixture was poured in ice-water, washed with 5% hydrochloric acid, 5% aqueous potassium hydroxide and water in the order, and dried over anhydrous sodium sulfate. Finally the solvent was distilled off under reduced pressure to give, as a colorless clear oil, the phosphate compound (34.5 g):

IR: $\nu_{max}$, cm$^{-1}$; 2900, 1720, 1680, 1365, 1160, 970.
NMR(CDCl$_3$): δ6.35(m, 3H×3, vinyl protons) 4.25(m, 4H×3, —CH$_2$CH$_2$—).

EXAMPLE 2

Using phosphorus oxychloride (16 g) and a solution of 2-hydroxyethyl methacrylate (34.8 g) and pyridine (36 g) in methylene chloride, the reaction and after-treatment procedure of Example 1 was repeated to give the phosphate compound (41.0 g):

IR: $\nu_{max}$, cm$^{-1}$; 2950, 1720, 1630, 1365, 1160, 980.
NMR(CDCl$_3$): δ6.10(bs, 1H×3, vinyl proton) 5.55(m, 1H×3, vinyl proton) 4.30(m, 4H×3, —CH$_2$CH$_2$—) 1.90(d, 3H×3, vinyl CH$_3$).

EXAMPLE 3

Using phosphorus oxychloride (16 g) and a solution of 2-hydroxypropyl methacrylate (34.8 g) and pyridine (36 g) in methylene chloride, the reaction and after-treatment procedure of Example 1 was repeated to give the phosphate compound (30.5 g):

IR: $\nu_{max}$, cm$^{-1}$: 2950, 1720, 1630, 1375, 1160, 1000.

NMR(CDCl$_3$): δ6.10(bs, 1H×3, vinyl proton) 5.55(m, 1H×3, vinyl proton) 4.85(m, 1H×3, —CH$_2$CHCH$_3$) 4.15(m, 2H×3, —CH$_2$CHCH$_3$) 1.90(d, 3H×3, vinyl CH$_3$) 1.30(m, 3H×3, —CH$_2$CHCH$_3$).

EXAMPLE 4

Using phosphorus oxychloride (16 g) and a solution of 2-chloro-3-hydroxypropyl methacrylate (45 g) and pyridine (36 g) in methylene chloride, the reaction and after-treatment procedure of Example 1 was repeated to give the phosphate compound (48.5 g):

IR: $\nu_{max}$, cm$^{-1}$: 2950, 1720, 1630, 1370, 1160, 1000, 760.

NMR(CDCl$_3$): δ 6.10(bs, 1H×3, vinyl proton) 5.50(m, 1H×3, vinyl proton) 4.20(m, 4H×3, —CH$_2$CH(Cl)CH$_2$) 3.65(m, 1H×3, —CH$_2$CH(Cl)CH$_2$) 1.90(d, 3H×3, vinyl CH$_3$).

EXAMPLE 5

Using phosphorus oxychloride (16 g) and a solution of allyl alcohol (17.4 g) and pyridine (36 g) in methylene chloride, the reaction and after-treatment procedure of Example 1 was repeated to give the phosphate compound (17.0 g):

IR: $\nu_{max}$, cm$^{-1}$: 2900, 1630, 1365, 1160, 980.

NMR(CDCl$_3$): δ 5.60(m, 2H×3, vinyl protons) 4.10(bs, 1H×3, vinyl proton) 3.50(t, 2H×3, —CH$_2$—).

EXAMPLE 6

A mixture of phenol (120 g), phosphorus oxychloride (180 g) and calcium chloride (25 g) was heated at 150° C. for 5 hours. After completion of the reaction, the excess phosphorus oxychloride was distilled off under reduced pressure to give the phosphoryl dichloride (221 g):

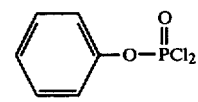

The above produce (211 g) was dissolved in methylene chloride (300 ml), the solution added dropwise to a solution of 2-hydroxyethyl methacrylate (240 g) and pyridine (160 g) in methylene chloride (400 ml) under cooling at 0° C., and the mixture stirred for 5 hours.

After completion of the reaction, the reaction mixture was washed with 5% hydrochloric acid, 5% aqueous potassium hydroxide and water in that order and dried over anhydrous sodium sulfate. Finally the solvent was distilled off under reduced pressure to give, as a colorless clear oil, the phosphate compound (350 g):

IR: $\nu_{max}$, cm$^{-1}$: 2900, 1720, 1630, 1600, 1365, 1160, 960.

NMR(CDCl$_3$): δ 7.35(s, 5H×1, arom, protons) 6.10(bs, 1H×2, vinyl proton) 5.55(m, 1H×2, vinyl proton) 4.25(m, 4H×2, —CH$_2$CH$_2$—) 1.90(d, 3H×2, vinyl CH$_3$).

EXAMPLE 7

Using o-chlorophenol (14 g), phosphorus oxychloride (18 g) and calcium chloride (2.5 g), the procedure of Example 6 was repeated to give the phosphoryl dichloride (26 g):

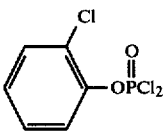

The above product (25 g) was further reacted with 2-hydroxypropyl methacrylate (28 g) and pyridine (16 g) and the reaction mixture worked up in the same manner as Example 6 to give the phosphate compound:

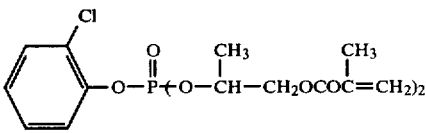

IR: $\nu_{max}$, cm$^{-1}$: 2950, 1720, 1630, 1600, 1370, 1160, 960.

NMR(CDCl$_3$): δ 7.20(m, 4H×1, arom. protons) 6.10(bs, 1H×2, vinyl proton) 5.55(m, 1H×2, vinyl proton)

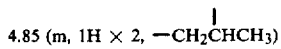

4.85 (m, 1H × 2, —CH$_2$CHCH$_3$)

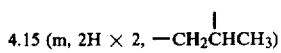

4.15 (m, 2H × 2, —CH$_2$CHCH$_3$)

1.90(d, 3H×2, vinyl CH$_3$) 1.30(m, 3H×2, —CH$_2$CHCH$_3$)

EXAMPLE 8

Using 4-tert-butylphenol (15 g), phosphorus oxychloride (16 g) and calcium chloride (2.5 g), the procedure of Example 6 was repeated to give the phosphoryl dichloride (26 g):

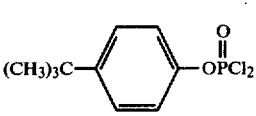

The above product (25.7 g) was further reacted with allyl alcohol (11.6 g) and pyridine (16 g) and the reaction mixture worked up in the same manner as Example 6 to give the phosphate compound (26.5 g):

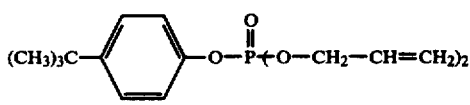

IR: $\nu_{max}$, cm$^{-1}$: 2950, 1630, 1600, 1365, 1160, 960.

NMR(CDCl$_3$): δ 6.95(ABq, 4H×1, arom. protons) 5.62(m, 2H×2, vinyl protons) 4.10(bs, 1H×2, vinyl proton) 3.50(t, 2H×2, —CH$_2$—) 1.25(s, 9H×1, tert-butyl).

EXAMPLE 9

Using beta-naphtol (16 g), phosphorus oxychloride (18 g) and calcium chloride (25 g), the procedure of Example 6 was repeated to give the phosphoryl dichloride (27 g):

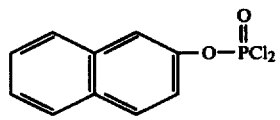

The above product (26 g) was further reacted with 2-hydroxyethyl acrylate (24 g) and pyridine (16 g) and the reaction mixture worked up in the same manner as Example 6 to give the phosphate compound (39.5 g):

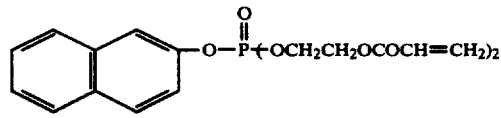

IR: $\nu_{max}$, cm$^{-1}$: 2900, 1720, 1630, 1600, 1365, 1160, 960.

NMR(CDCl$_3$): δ 7.80–7.05(m, 7H×;, arom. protons) 6.35(m, 3H×2, vinyl protons) 4.25(m, 4H×2, —CH$_2$CH$_2$—).

EXAMPLE 10

Using 7-methoxy-α-naphthol (19 g), phosphorus oxychloride (18 g) and calcium chloride (2.5 g), the procedure of Example 6 was repeated to give the phosphoryl dichloride (29 g):

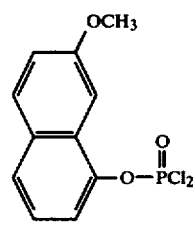

The above product (29 g) was further reacted with 2-hydroxyethyl methacrylate (24 g) and pyridine (16 g) and the reaction mixture worked up in the same manner as Example 6 to give the phosphate compound (45.4 g):

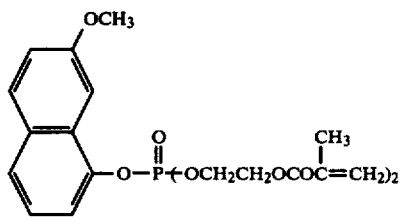

IR: $\nu_{max}$, cm$^{-1}$: 2950, 1720, 1630, 1600, 1365, 1160, 970.

NMR(CDCl$_3$): δ 7.70–6.70(m, 6H×1, arom. protons) 6.10(bs, 1H×2, vinyl proton) 5.55(m, 1H×2, vinyl proton) 4.25(m, 4H×2, —CH$_2$CH$_2$—) 3.90(s, 3H×1, —OCH$_3$) 1.90(d, 3H×2, vinyl CH$_3$).

EXAMPLE 11

Using o-cresol (10.8 g), phosphorus oxychloride (16 g) and calcium chloride (2.5 g), the procedure of Example 6 was repeated to give the phosphoryl dichloride (22 g):

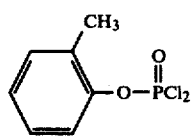

The above product (22 g) was further reacted with 2-chloro-3-hydroxypropyl methacrylate (35.6 g) and pyridine (16 g) and the reaction mixture worked up in the same manner as Example 6 to give the phosphate compound (47 g):

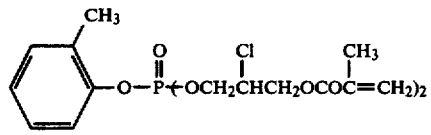

IR: $\nu_{max}$, cm$^{-1}$: 2950, 1720, 1630, 1600, 1370, 1160, 1000, 760.

NMR(CDCl$_3$): δ 6.85(m, 4H×1, arom. protons) 6.10(bs, 1H×2, vinyl proton) 5.55(m, 1H×2, vinyl proton) 3.65(m, 1H×2, —CH$_2$CH(Cl)CH$_2$—) 4.20(m, 4H×2, —CH$_2$CH(Cl)CH$_2$—) 2.20(s, 3H×1, —CH$_3$) 1.90(d, 3H×2, vinyl CH$_3$).

EXAMPLE 12

Using 4-bromoresorcinol (18.9 g) phosphorus oxychloride (32 g) and calcium chloride (5 g), the procedure of Example 6 was repeated to give the phosphoryl dichloride (43 g):

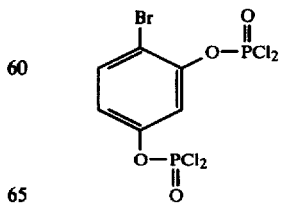

The above product (42 g) was further reacted with 2-hydroxypropyl methacrylate (57.5 g) and pyridine (32 g) and the reaction mixture worked up in the same manner as Example 6 to give the phosphate compound (81 g):

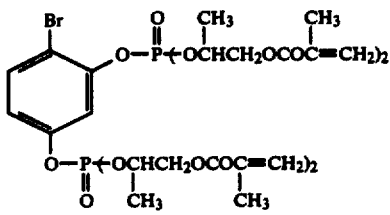

IR: $\nu_{max}$, cm$^{-1}$: 2950, 1720, 1630, 1600, 1370, 1160, 960.

NMR(CDCl$_3$): δ 7.40(d, 1H×1, arom. proton) 6.40(m, 2H×1, arom. protons) 6.10(bs, 1H×4, vinyl proton) 5.55(m, 1H×4, vinyl proton) 4.85(m, 1H×4, —CH$_2$CHCH$_3$) 4.15(m, 2H×4, —CH$_2$CHCH$_3$) 1.93(d, 3H×4, vinyl CH$_3$) 1.93(m, 3H×4, —CH$_2$CHCH$_3$).

EXAMPLE 13

Using 1,3-dihydroxynaphhalene (16 g), phosphorus oxychloride (32 g) and calcium chloride (5 g), the procedure of Example 6 was repeated to give the phosphoryl dichloride (39 g):

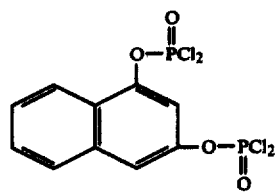

The above product (39 g) was further reacted with 2-hydroxyethyl methacrylate (48 g) and pyridine (32 g) and the reaction mixture worked up in the same manner as Example 6 to give the phosphate compound (73.0 g):

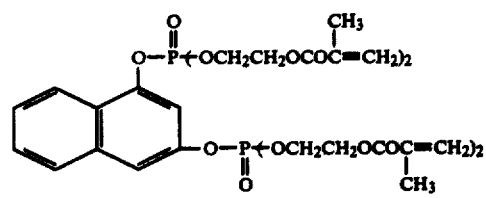

IR: $\nu_{max}$, cm$^{-1}$: 2950, 1720, 1630, 1600, 1365, 1160, 960.

NMR(CDCl$_3$): δ 8.00–6.80(m, 6H×1, arom. protons) 6.10(bs, 1H×4, vinyl proton) 5.55(m, 1H×4, vinyl proton) 4.25(m, 4H×4, —CH$_2$CH$_2$—) 1.90(d, 3H×4, vinyl CH$_3$).

EXAMPLE 14

Using bisphenol A (34 g), phosphorus oxychloride (35 g) and calcium chloride (5 g), the procedure of Example 6 was repeated to give the phosphoryl dichloride (57 g):

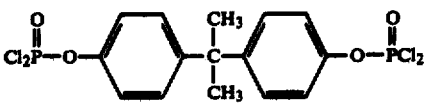

The above product (39 g) was further reacted with 2-hydroxyethyl acrylate (48 g) and pyridine (32 g) and the reaction mixture worked up in the same manner as Example 6 to give the phosphate compound (72 g):

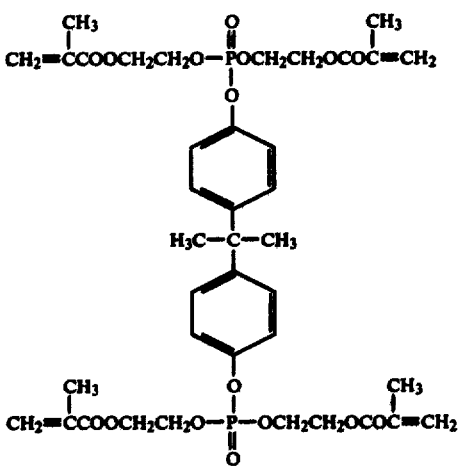

IR: $\nu_{max}$, cm$^{-1}$: 2950, 1720, 1630, 1600, 1365, 1295, 960.

NMR(CDCl$_3$): δ 7.10(s, 4H×2, arom. protons) 6.10(bs, 1H×4, vinyl proton) 5.55(m, 1H×4, vinyl proton) 4.35(m, 4H×4, —CH$_2$CH$_2$—) 1.90(d, 3H×4, vinyl CH$_3$) 1.70(s, 3H×2, —CH$_3$).

EXAMPLE 15

Phosphoryl dichloride (39 g) as obtained in Example 14 was reacted with 2-hydroxypropyl methacrylate (58 g) and pyridine (32 g) and the reaction mixture worked up in the same manner as Example 6 to give the phosphate compound (74 g):

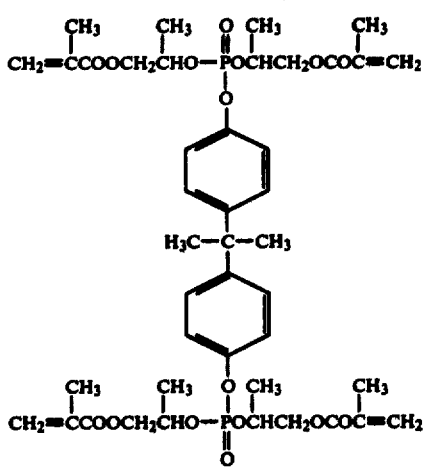

(IR: $\nu_{max}$, cm$^{-1}$: 2950, 1720, 1630, 1600, 1370, 1290, 980.

NMR(CDCl$_3$): δ 7.10(s, 4H×2, arom. protons) 6.10(bs, 1H×4, vinyl proton) 5.55(m, 1H×4, vinyl proton) 4.85(m, 1H×4, —CH$_2$CHCH$_3$) 4.15(m, 2H×4, —CH$_2$CHCH$_2$) 1.90(d, 3H×4, vinyl CH$_2$) 1.70(m, 3H×2, —CH$_3$) 1.30(m, 3H×4, —CH$_2$CHCH$_3$)

EXAMPLE 16

Using 3-chloro-4,4'-dihydroxybiphenyl (33 g), phosphorus oxychloride (32 g) and calcium chloride (5 g), the procedure of Example 6 was repeated to give the phosphoryl dichloride (55 g):

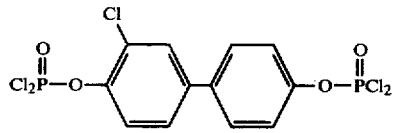

The above product (38 g) was further reacted with 2-hydroxyethyl acrylate (48 g) and pyridine (32 g) and the reaction mixture worked up in the same manner as Example 6 to give the phosphate compound:

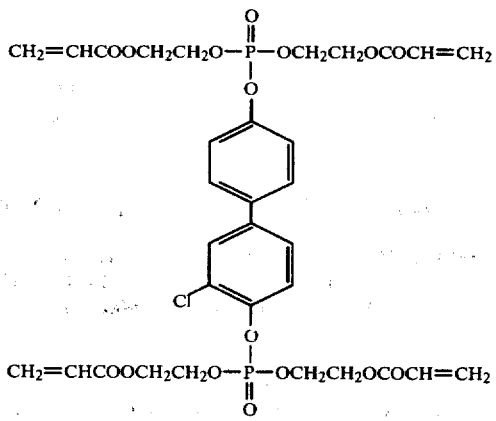

IR: $\nu_{max}$, cm$^{-1}$: 2950, 1720, 1630, 1600, 1365, 1295, 960, 845.

NMR(CDCl$_3$): δ 7.30(m, 3H×1, arom. protons) 7.10(s, 4H×1, arom. protons) 6.35(m, 3H×4, vinyl protons) 4.25(m, 4H×4, —CH$_2$CH$_2$—)

EXAMPLE 17

Using bis(4-hydroxyphenyl)phenylmethane (28 g), phosphorus oxychloride (33 g) and calcium chloride (5 g), the procedure of Example 6 was repeated to give the phosphoryl dichloride (37 g):

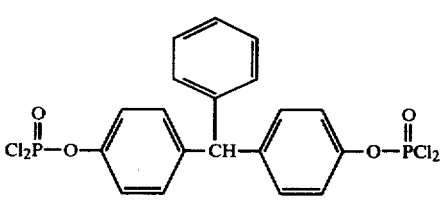

The above product (84 g) was further reacted with allyl alcohol (22 g) and pyridine (32 g) and the reaction mixture worked up in the same manner as Example 6 to give the phosphate compound (45 g):

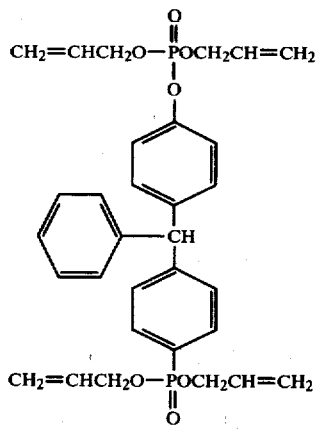

IR: $\nu_{max}$, cm$^{-1}$: 3050, 2900, 1630, 1600, 1365, 1295, 960.

NMR(CDCl$_3$): δ 7.10(m, 13H×1, arom. protons) 5.62(m, 2H×4, vinyl protons)

5.60(s, 1H × 1, —CH)

4.10(bs, 1H×4, vinyl proton) 3.50(t, 2H×4, —CH$_2$—)

EXAMPLE 18

Using bis(4-hydroxyphenyl) ether (20 g), phosphorus oxychloride (32 g) and calcium chloride (5 g), the procedure of Example 6 was repeated to give the phosphoryl dichloride (41 g):

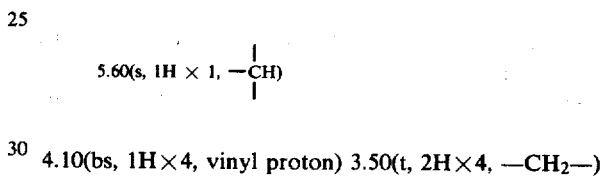

The above product (41 g) was further reacted with allyl alcohol (22 g) and pyridine (32 g) and the reaction mixture worked up in the same manner as Example 6 to give the phosphate compound (40 g):

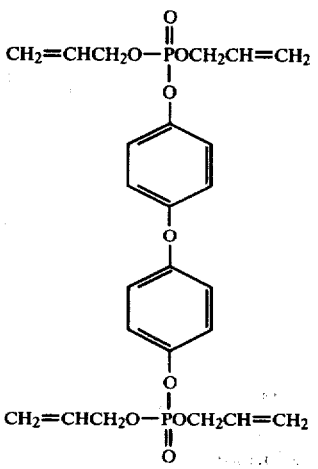

IR: $\nu_{max}$, cm$^{-1}$: 2900, 1630, 1600, 1365, 1295, 1100, 960.

NMR(CDCl$_3$): δ 7.10(s, 4H×2, arom. protons) 5.60(m, 2H×4, vinyl protons) 4.10(bs, 1H×4, vinyl proton) 3.50(t, 2H×4, —CH$_2$—).

Examples of use of the above compounds will be given below.

PREPARATION EXAMPLE 1

A fused quartz sand was comminuted in a ceramic ball mill to prepare a quartz powder passed through a 200-mesh sieve γ-methacryloxypropyltrimethoxysilane in an amount corresponding to 0.5 wt.% with respect to the weight of quartz powder was added to an aqueous solution of sodium hydroxide having a pH of 9.0-9.8 and dissolved therein with stirring. The quartz powder prepared above was then added to the mixture, and the resulting mixture was thoroughly blended and stirred to obtain a slurry. The slurry was dried at 130° C. to obtain a quartz powder treated with silane.

The phosphate compound prepared in Example 14 (70 parts by weight) and the phosphate compound prepared in Example 1 (30 parts by weight) were mixed to obtain a resin binder. To the resulting binder (20 parts by weight) were added the silane-treated quartz powder (80 parts by weight) and colloidal silica (3 parts by weight) and the mixture was thoroughly blended to prepare a paste.

The paste was divided into two equal portions. To one portion of the paste was added 0.6 parts by weight of N,N'-dimethyl-p-toluidine and 2 parts by weight of p-tolylsulfonylhydrazine per 100 parts by weight of the paste, and the mixture was thoroughly blended to obtain a uniform dispersion. To the other portion of the paste was added 0.8 part by weight of benzoyl peroxide per 100 parts by weight of the paste, and the mixture was thoroughly blended to obtain a uniform dispersion.

The resulting dispersions were then blended in an equal proportion and the operability and physical properties of the resulting mixture was tested. The results obtained are shown in Table 1 below.

PREPARATION EXAMPLE 2

In the same manner as described in Preparation Example 1, the phosphate prepared in Example 6 (80 parts by weight) and ethylene glycol dimethacrylate (20 parts by weight) were blended to obtain a resin binder. The silane-treated quartz powder (85 parts by weight) and other additives were added to the resulting binder (15 parts by weight) to prepare a uniform dispersion in the same manner as described in Preparation Example 1. The operability and physical properties of the resulting mixture were tested, and the results obtained are also shown in Table 1 below.

PREPARATION EXAMPLE 3

In the same manner as described in Preparation Example 1, the phosphate prepared in Example 13 (75 parts by weight) and diethylene glycol dimethacrylate (25 parts by weight) were blended to obtain a resin binder. The silane-treated quartz powder (80 parts by weight) and other additives were added to the resulting binder (20 parts by weight) to prepare a uniform dispersion in the same manner as described in Preparation Example 1. The operability and physical properties of the resulting mixture were tested, and the results obtained are also shown in Table 1 below.

PREPARATION EXAMPLE 4

In the same manner as described in Preparation Example 1, the phosphate prepared in Example 14 (70 parts by weight) and triethylene glycol dimethacrylate (30 parts by weight) were blended to obtain a resin binder. The silane-treated quartz powder (80 parts by weight) and other additives were added to the resulting binder (20 parts by weight) to prepare a uniform dispersion in the same manner as described in Preparation Example 1. The operability and physical properties of the resulting mixture were tested, and the results obtained are also shown in Table 1 below.

COMPARATIVE EXAMPLE

In the same formulation as used in Preparation Example 4, a known bisphenyl A diglycidyl methacrylate was used in place of the phosphate to prepare a uniform dispersion. The operability and physical properties of the resulting mixture were tested, and the results obtained are also shown in Table 1 below.

TABLE 1

| Test Item* | Preparation Example 1 | Preparation Example 2 | Preparation Example 3 | Preparation Example 4 | Comparative Example |
|---|---|---|---|---|---|
| Gelation Time (min.) | 3.5 | 3.5 | 3.5 | 3.5 | 3.5 |
| Curing Time (min.) | 4.5 | 4.5 | 4.5 | 4.5 | 4.5 |
| Tensile Strength (MPa) | 65.0 | 52.5 | 63.9 | 64.6 | 49.5 |
| Compression Strength (MPa) | 347.5 | 323.0 | 350.0 | 351.8 | 298.6 |
| Bending Strength (MPa)** | 177.9 | 118.7 | 170.2 | 173.9 | 110.0 |
| Elastic Coefficient (MPa) × 10$^2$*** | 299.2 | 201.9 | 284.5 | 296.0 | 191.3 |
| Thermal Expansion (cm/cm/°C.) × 10$^{-6}$ | 35.4 | 35.0 | 35.5 | 35.8 | 36.0 |
| Rockwell Hardness (H$_R$H) | 112 | 118 | 111 | 114 | 99 |
| Knoop Hardness (50 g, 5 sec.) | 86 | 89 | 85 | 86 | 79 |
| Amount of Water Absorption (mg/cm$^2$) | 0.41 | 0.37 | 0.42 | 0.40 | 0.44 |

*According to American Dental Association Specification No. 27
** According to International Standard, ISO-4049
***Calculated according to JIS K-6705

What is claimed is:

1. A phosphate derivative represented by the formula (I)

wherein A represents an aryl group which may be substituted with one or more substituents selected from the group consisting of an alkenyl group, an acryloyloxy group, a methacryloyloxy, an aryl group, a halogen atom, an alkyl group, an alkoxy group, a hydroxy group substituted with an aryl group and a group of the formula

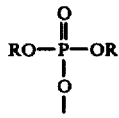

in which each of said substituents may further be substituted with one or more aryl groups or halogen atoms, and any aryl group as a substituent of the group A may be substituted with a substituent selected from the group consisting of an alkenyl group, an acryloyloxy group, a methacryloyloxy group and a group of the formula

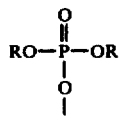

and R's may be the same or different and each represents an alkenyl group, an alkenylaryl group, an acryloyloxy(lower)alkyl group, an acryloyloxyaryl group, a methacryloyloxy(lower)alkyl group or a methacryloyloxyaryl group in which the (lower)alkyl group and aryl group may be substituted with a halogen atom, there being two

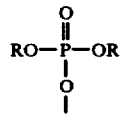

groups in the phosphate derivative, including that present in formula (I).

2. The phosphate derivative according to claim 1, wherein A represents an aryl group substituted with the group of the formula

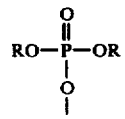

wherein R is as defined in claim 1.

3. The phosphate derivative according to claim 2, wherein said aryl group is substituted with a halogen atom.

4. The phosphate derivative according to claim 1, wherein A represents an aryl group having an aryl-substituted alkyl group substituted with a group of the formula

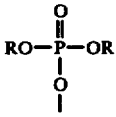

wherein R is as defined in claim 1.

5. The phosphate derivative according to claim 1, wherein A represents an aryl group having an aryl group substituted with a group of the formula

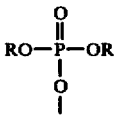

wherein R is as defined above, and with a halogen atom.

6. The phosphate derivative according to claim 1, wherein A represents an aryl group having an alkyl group substituted with an aryl group having a group of the formula

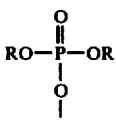

wherein R is as defined above, and with an aryl group which does not contain the group of the formula above.

7. The phosphate derivative according to claim 1, wherein A represents an aryl group having a hydroxy group substituted with an aryl group having a group of the formula

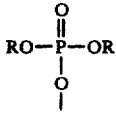

wherein R is as defined above.

8. A process for producing the phosphate derivative of claim 1 which comprises reacting a compound represented by the formula

A—OH wherein A is as defined above, with a phosphorus oxyhalide to produce a compound of the formula

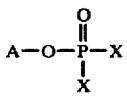

wherein X is represents a halogen atom, and reacting the resulting compound with a compound of the formula

R—OH wherein R is as defined above; or reacting a compound of the formula

A—OH wherein A is as defined above, with a compound of the formula

R—OH wherein R is as defined above, in the presence of a phosphorus oxyhalide.

9. A filler for human hard tissues comprising at least one phosphate derivative, or a polymer obtained by polymerizing at least one phosphate derivative as a polymerizable monomer, or a mixture thereof, said phosphate derivative being represented by the formula (I)

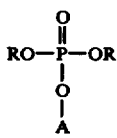
(I)

wherein A represents an aryl group which may be substituted with one or more substituents selected from the group consisting of an alkenyl group, an acryloyloxy group, a methacryloyloxy, an aryl group, a halogen atom, an alkyl group, an alkoxy gorup, a hydroxy group substituted with an aryl group and a group of the formula

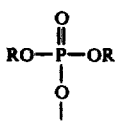

in which each of said substituents may further be substituted with one or more aryl groups or halogen atoms, and any aryl group as a substituent of the group A may be substituted with a substituent selected from the group consisting of an alkenyl group, an acryloyloxy group, a methacryloyloxy group and a group of the formula

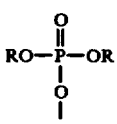

and R's may be the same or different and each represents an alkenyl group, an alkenylaryl group, an acryloyloxy(lower)alkyl group, and acryloyloxyaryl group, a methacryloyloxy(lower)alkyl group or a methacryloyloxyaryl group in which the (lower)alkyl group and aryl group may be substituted with a halogen atom, there being two

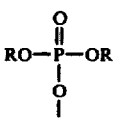

groups in the phosphate, including that present in formula (I).

10. The phosphate derivative according to claim 2 which is:

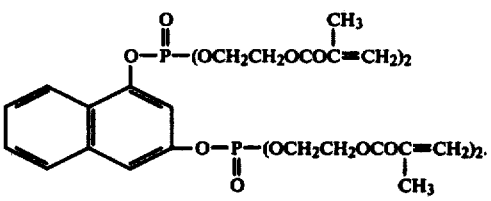

11. The phosphate derivative according to claim 7 which is:

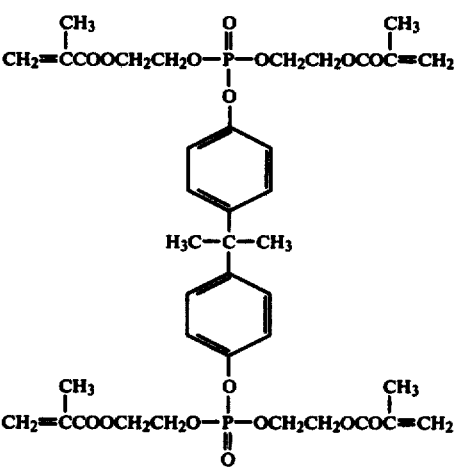

12. A filler for human hard tissue according to claim 9 which comprises two polymerizable monomers one of which is a phosphate derivative as defined in claim 9 and the other of which is a different phosphate derivative as defined in claim 9 or is ethylene glycol dimethacrylate, diethylene glycol dimethacrylate or triethylene glycol dimethacrylate.

13. A filler for human hard tissue according to claim 9 comprising a mixture of a phosphate compound having the formula:

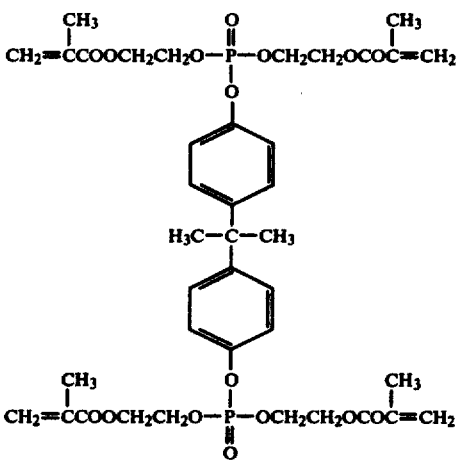

with a phosphate compound having the formula $(CH_2=CHCOOCH_2CH_2O)_3P=O$.

14. A filler for human hard tissue according to claim 13 which additionally includes silane-treated quartz powder and colloidal silica to form a paste, a curing agent and a reaction promoter.

15. The phosphate derivative according to claim 6 which is:

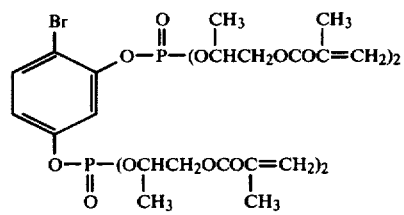

16. The phosphate derivative according to claim 4 which is:

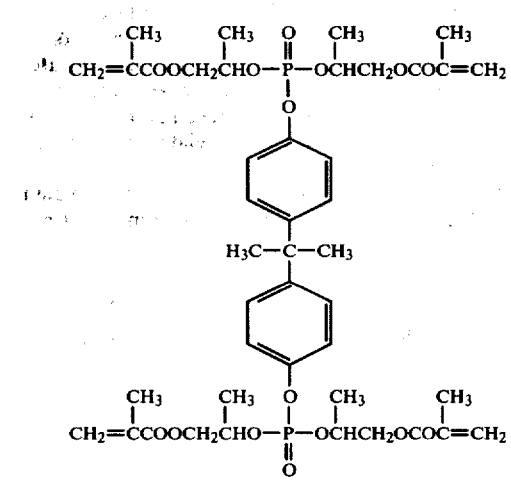

17. The phosphate derivative according to claim 5 which is:

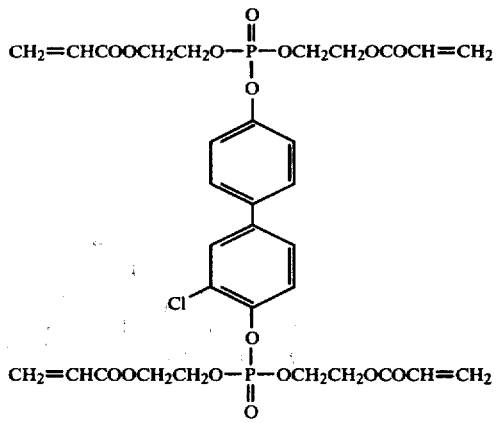

18. The phosphate derivative of claim 6 which is

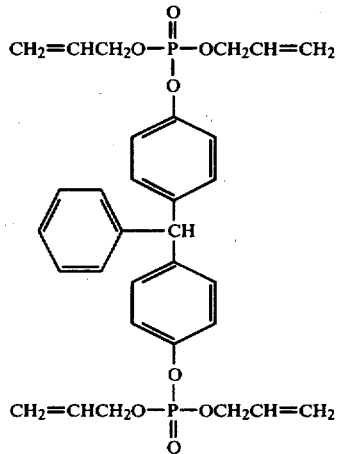

19. The phosphate derivative of claim 7 which is:

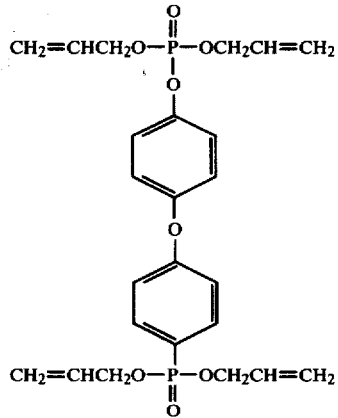

* * * * *